(12) United States Patent
Mabkhot et al.

(10) Patent No.: US 10,501,426 B1
(45) Date of Patent: Dec. 10, 2019

(54) SYNTHESIS OF THIAZOLE DERIVATIVE AS ANTICANCER AND ANTI-ANTIBIOTICS RESISTANT BACTERIA AGENT

(71) Applicant: KING SAUD UNIVERSITY, Riyadh (SA)

(72) Inventors: Yahia Nasser Mabkhot, Abha (SA); Jamal Mohammed Ali Khaled, Riyadh (SA); Naiyf Sultan Helial Alaloi Alharbi, Riyadh (SA); Fahd Ali Nasr Mohammed, Riyadh (SA); Fahd Abdo Almekhlafi, Riyadh (SA); Nael Mahmmoud Abutaha, Riyadh (SA); Salim S. Al-Showiman, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/246,047

(22) Filed: Jan. 11, 2019

(51) Int. Cl.
*C07D 277/16* (2006.01)
*A01N 25/08* (2006.01)
*A01N 43/78* (2006.01)
*A61P 35/00* (2006.01)
*A61P 31/04* (2006.01)

(52) U.S. Cl.
CPC ............ *C07D 277/16* (2013.01); *A61P 31/04* (2018.01); *A61P 35/00* (2018.01); *A01N 25/08* (2013.01); *A01N 43/78* (2013.01)

(58) Field of Classification Search
CPC ........ C07D 277/16; A61P 31/04; A61P 35/00; A01N 25/08; A01N 43/78
See application file for complete search history.

(56) References Cited

U.S. PATENT DOCUMENTS

| 6,420,415 B1 | 7/2002 | Yamashita et al. |
| 7,169,937 B2 | 1/2007 | Achten et al. |
| 7,235,687 B2 | 6/2007 | Fournie-Zaluski et al. |
| 9,340,497 B2 | 5/2016 | Balavoine et al. |
| 2015/0196546 A1 | 7/2015 | Zhou et al. |

FOREIGN PATENT DOCUMENTS

WO    WO 2017/027557 A1    2/2017

OTHER PUBLICATIONS

Golub et al. Science (1999), vol. 286, 531-537.*
El-Desoky et al., "Synthesis of some new thiazole derivatives of pharmaceutical interest," Sulfur Letters, vol. 26, 2003-Issue, pp. 127-135.

* cited by examiner

*Primary Examiner* — Rebecca L Anderson
(74) *Attorney, Agent, or Firm* — Richard C. Litman; Nath, Goldberg & Meyer

(57) ABSTRACT

A thiazole derivative compound includes a compound having the following structural formula:

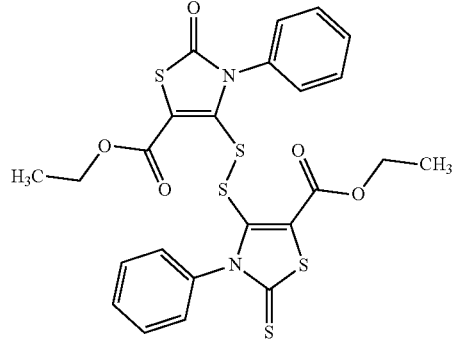

or a pharmaceutically acceptable salt thereof.

11 Claims, 5 Drawing Sheets

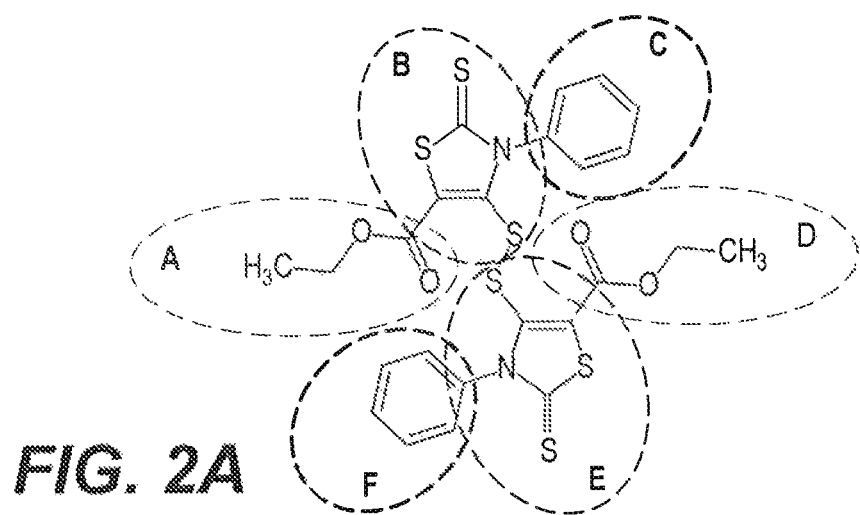
FIG. 2A
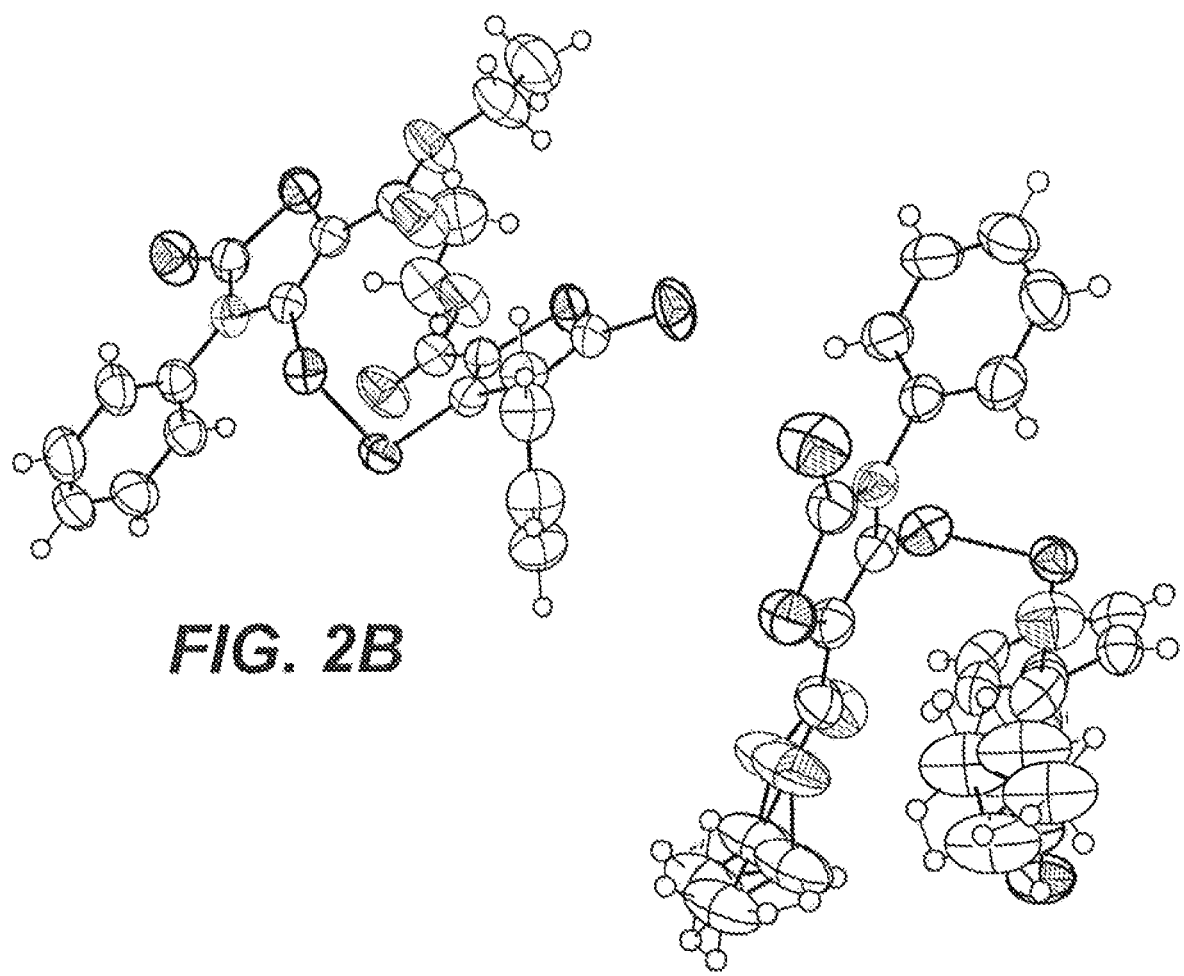
FIG. 2B
FIG. 2C

US 10,501,426 B1

SYNTHESIS OF THIAZOLE DERIVATIVE AS ANTICANCER AND ANTI-ANTIBIOTICS RESISTANT BACTERIA AGENT

BACKGROUND

1. Field

The disclosure of the present patent application relates to anticancer, antimicrobial and larvicidal agents, and particularly to a thiazole derivative for use against cancer, antibiotic-resistant bacteria and larval infestation. The present inventors acknowledge the additional funding received from King Khalid University for research relating to the subject matter described herein.

2. Description of the Related Art

Many compounds characterized by skeletons containing a thiazole ring exhibit biologically beneficial activities, such as anticonvulsant, antimicrobial, anti-inflammatory, anticancer, antidiabetic, anti-HIV, anti-Alzheimer, antihypertensive, and antioxidant activities.

Toxic side effects of existing marketed drugs, the development of drug resistance and increasing incidence of infection caused by rapid development of microbial resistance to most known antibiotics drive a constant need for new drug development. Synthesis of new compounds as antimicrobial agents against antibiotic-resistant bacteria, for example, is becoming increasingly important. At the same time, cancer is one of the most prevalent diseases in the world. In 2015, there were 17.5 million new cancer cases and over 8.7 million deaths worldwide. Therefore, discovering and synthesizing new compounds effective against both antibiotic-resistant bacteria and cancer is an urgent and perpetual task.

SUMMARY

A thiazole derivative compound (referred to hereinafter as the thiazole derivative compound or compound 6, interchangeably) has the following structural formula

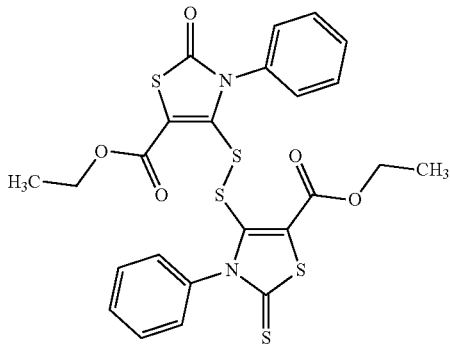 [SMILES: CCOC(=O)c1sc(=O)n(-c2ccccc2)c1SSc1c(C(=O)OCC)sc(=S)n1-c1ccccc1]

Compound 6

The thiazole derivative compound provides antitumor, antibiotic and larvicidal activities, as disclosed herein. The thiazole derivative compound may be synthesized by reacting diethyl 2,2'-(thiocarbonylbis(sulfanediyl)diacetate (precursor 1) with phenyl isothiocyanate (precursor 2), affording a precipitate comprising the thiazole derivative compound.

These and other features of the present disclosure will become readily apparent upon further review of the following specification and drawings.

BRIEF DESCRIPTION OF THE DRAWINGS

FIG. 2A shows the X-ray crystal verified structure of compound 6 with labeled components A-F; FIGS. 2B-2C depict Oak Ridge Thermal Ellipsoid Plot (ORTEP) generated models of compound 6, drawn at 50% probability level with H-atoms as small circles of arbitrary level.

Similar reference characters denote corresponding features consistently throughout the attached drawings.

DETAILED DESCRIPTION OF THE PREFERRED EMBODIMENTS

A thiazole derivative compound can be represented by the following structural formula:

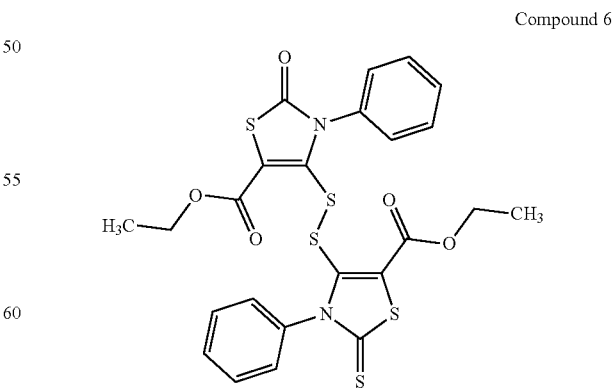

Compound 6 or a pharmaceutically acceptable salt thereof.

A method for preparing the thiazole derivative compound includes reacting diethyl 2,2'-(thiocarbonylbis(sulfanediyl)

diacetate (precursor 1) (Soleiman-Beigi and Taherinia, 2014) with phenyl isothiocyanate (precursor 2) in the presence of $K_2CO_3$ in an organic solvent to afford a precipitate comprising the thiazole derivative compound, compound 6.

In an embodiment, the thiazole derivative compound is an anticancer agent. In an embodiment, the thiazole derivative compound is an antimicrobial agent.

Figure 1:
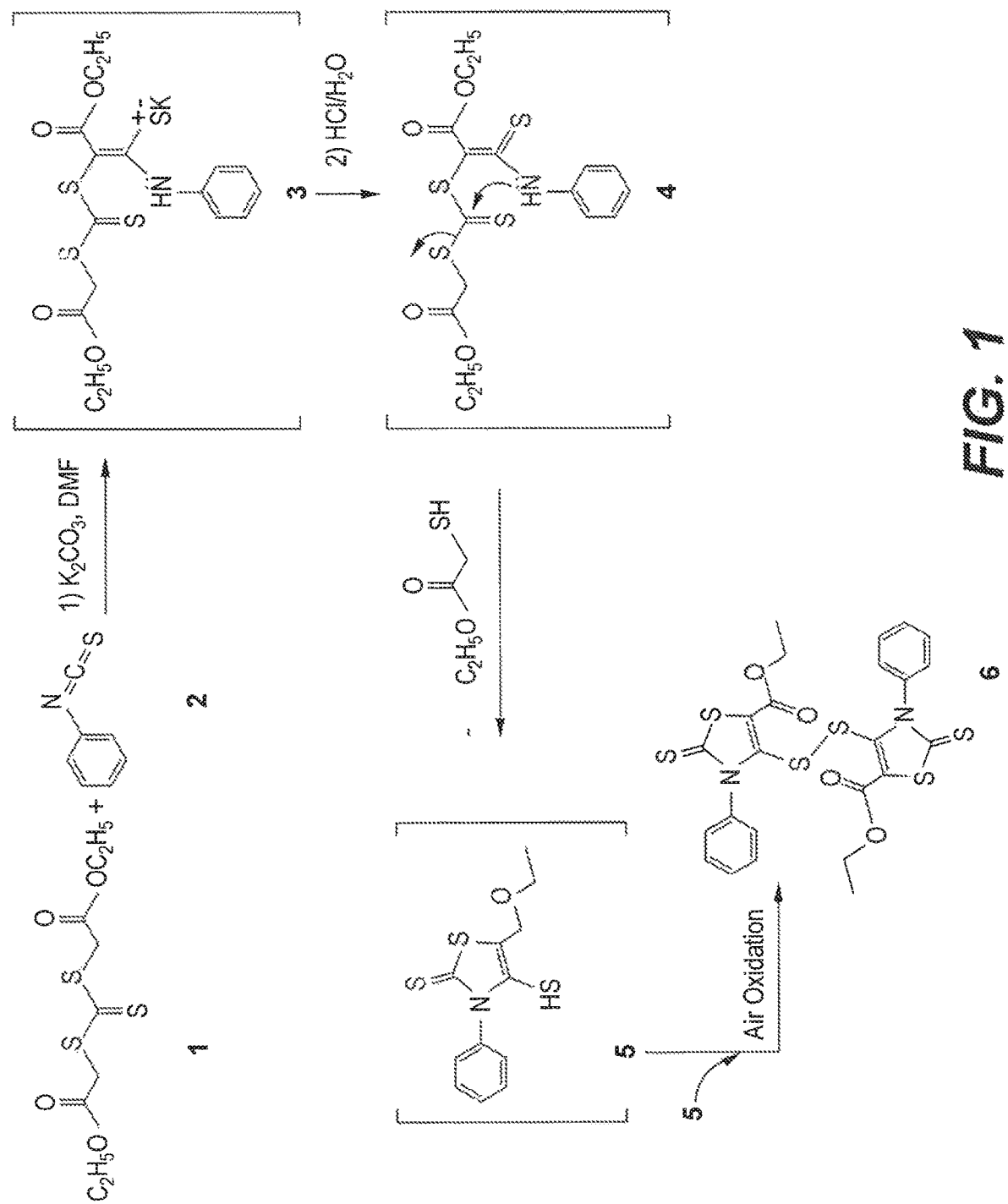
FIG. 1 shows an exemplary reaction scheme for synthesizing compound 6.

An exemplary method of synthesizing the thiazole derivative compound is depicted in FIG. 1. As shown in FIG. 1, diethyl 2,2'-(thiocarbonylbis(sulfanediyl)diacetate 1 can be mixed with phenyl isothiocyanate 2 in an organic solvent, such as dimethyl formamide (DMF), at room temperature to form a first mixture. Anhydrous potassium carbonate ($K_2CO_3$) can be mixed with the first mixture to form a second mixture. The second mixture can be pH adjusted, for example by addition of hydrochloric acid (HCl), e.g., aqueous solution of hydrochloric acid, to precipiate a solid product including the thiazole derivative compound, for example, by air oxidation. The product can be collected by filtration, washed, and dried.

An embodiment of the present subject matter is directed to a method of treating a disease comprising administering a therapeutically effective amount of the thiazole derivative compound to a patient afflicted by the disease. In an embodiment, the disease comprises cancer. The cancer may be liver cancer, colon cancer or breast cancer. In an embodiment, the disease is caused by bacteria, such as a gram positive bacteria or gram negative bacteria.

A pharmaceutical composition can include the thiazole derivative compound and a pharmaceutically acceptable carrier. The pharmaceutical composition can be administered to a patient by any suitable route for treating or inhibiting bacterial infections, fungal infections, and/or cancer. Parenteral, otic, ophthalmic, nasal, inhalable, buccal, sublingual, enteral, topical, oral, peroral, and injectable dosage forms are particularly useful. Particular dosage forms include solid or liquid dosage forms. Exemplary suitable dosage forms include tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

The amount of thiazole derivative compound incorporated in a dose can be selected according to the examples provided herein and/or according to known principles of pharmacy. An effective amount or therapeutically effective amount of the thiazole derivative compound is specifically contemplated. A therapeutically effective amount is the amount or quantity of active ingredient which is enough for the required or desired therapeutic response, or in other words, the amount, which is sufficient to elicit an appreciable biological response when administered to a patient. The appreciable biological response, i.e., anti-microbial activities or anticancer activities, can occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors.

The thiazole derivative compound can have larvicidal activities, and is particularly effective against mosquito larvae. As such, additional embodiments of the present subject matter include a larvicidal active composition. A method of preventing or inhibiting the growth of mosquitoes can include the step of applying the larvicidal active composition to a locus infested by mosquitoes or larvae or eggs thereof or to a locus exposed to such infestation.

The thiazole derivative compound having structure 6 was confirmed using different spectroscopic techniques, including infrared (IR) spectroscopy, hydrogen-1 nuclear magnetic resonance ($^1$H-NMR), carbon-13 nuclear magnetic resonance ($^{13}$C-NMR), distortionless enhancement by polarization transfer (DEPT) and high resolution mass-spectroscopy (HRMS). For example, in the IR spectrum, an ester carbonyl group appears at ν 1722 cm$^{-1}$, slightly shifted relative to the absorption peak of the ester carbonyl of the precursor 1, which appears at ν 1732 cm$^{-1}$. The $^1$H NMR spectrum of the product 6 reveals triplet and quartet signals of ethoxycarbonyl protons at δ 1.36 and 4.33 ppm (J=7 Hz). The aliphatic region of the $^{13}$C-NMR spectrum contains two peaks δ 14.30 and 62.86 ppm representing protons of the ester group; a peak at δ 137.12 ppm representing the olefinic carbon of the newly formed thiazole ring (N—C—S); and a peak at δ 189.55 ppm representing the thiocarbonyl carbon (—N—(C=S)—S), shifted from the corresponding peak at δ 220.2 ppm of precursor 1, consistent with the substitution of an N atom in place of the S atom, (—S—(C=S)—S) of precursor 1.

Without being bound by theory, the reaction mechanism is postulated to start via nucleophilic attack by the methylene group of precursor 1 to the thiocarbonyl of precursor 2, resulting in the formation of intermediate 3. Neutralization affords intermediate 4, which eliminates ethyl 2-mercaptoacetate to afford intermediate 5. Air oxidation of sulfhydryl groups of two molecules of intermediate 5 leads to formation of the bis-product of compound 6 (FIG. 1).

The crystallographic details of ethyl 5-(ethylsulfanyl)-2-thioxo-1,3-dithiolane-4-carboxylate (intermediate 5) are given in Table 1 and shown in FIGS. 2A-2C and FIGS. 3A-3B. Computer programs used for these analyses include: APEX2 (Bruker, 2007), SAINT (Bruker, 2007), SHELXS97 (Sheldrick, 2008), SHELXL2014/6 (Sheldrick, 2015), ORTEP-3 for Windows (Farrugia, 1997) and PLATON (Spek, 2009), WinGX (Farrugia, 1999) and PLATON (Spek, 2009).

TABLE 1

| AY842SA | |
|---|---|
| Crystal data | |
| Chemical formula | $C_8H_{10}O_2S_4$ |
| $M_r$ | 266.40 |
| Crystal system, space group | Monoclinic, $P2_1/c$ |
| Temperature (K) | 296 |
| a, b, c (Å) | 15.208 (4), 10.880 (3), 7.4779 (19) |
| β (°) | 103.954 (8) |
| V (Å$^3$) | 1200.8 (5) |
| Z | 4 |
| Radiation type | Mo Kα |
| μ (mm$^{-1}$) | 0.76 |
| Crystal size (mm) | 0.38 × 0.28 × 0.24 |
| Data collection | |
| Diffractometer | Bruker Kappa APEXII CCD |
| Absorption correction | Multi-scan (SADABS; Bruker, 2005) |
| $T_{min}$, $T_{max}$ | 0.740, 0.850 |
| No. of measured, independent and observed [I > 2σ(I)] reflections | 7022, 2756, 1643 |

TABLE 1-continued

AY842SA

| | |
|---|---|
| $R_{int}$ | 0.042 |
| $(\sin \theta/\lambda)_{max}$ (Å$^{-1}$) | 0.652 |
| Refinement | |
| $R[F^2 > 2\sigma(F^2)]$, $wR(F^2)$, S | 0.057, 0.150, 1.03 |
| No. of reflections | 2756 |
| No. of parameters | 129 |
| H-atom treatment | H-atom parameters constrained |
| $\Delta\rho_{max}, \Delta\rho_{min}$ (e Å$^{-3}$) | 0.56, −0.41 |

Figure 3A:
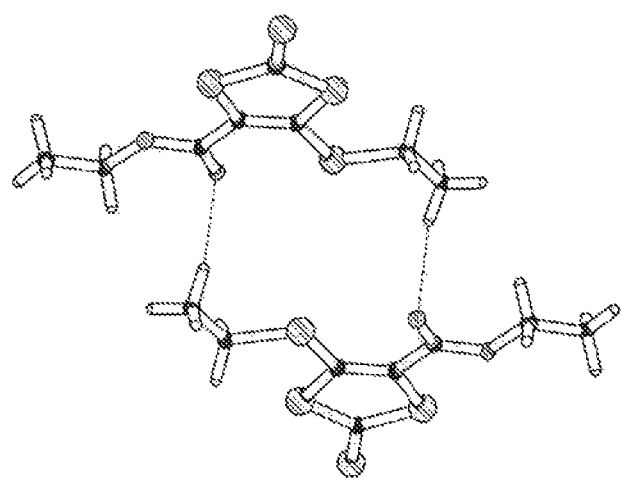
FIG. 3A shows modeled results of crystal packing of compound 6 depicting pairwise interactions between adjacent molecules of compound 6, where dotted lines represent the H-interactions.
Figure 3B:
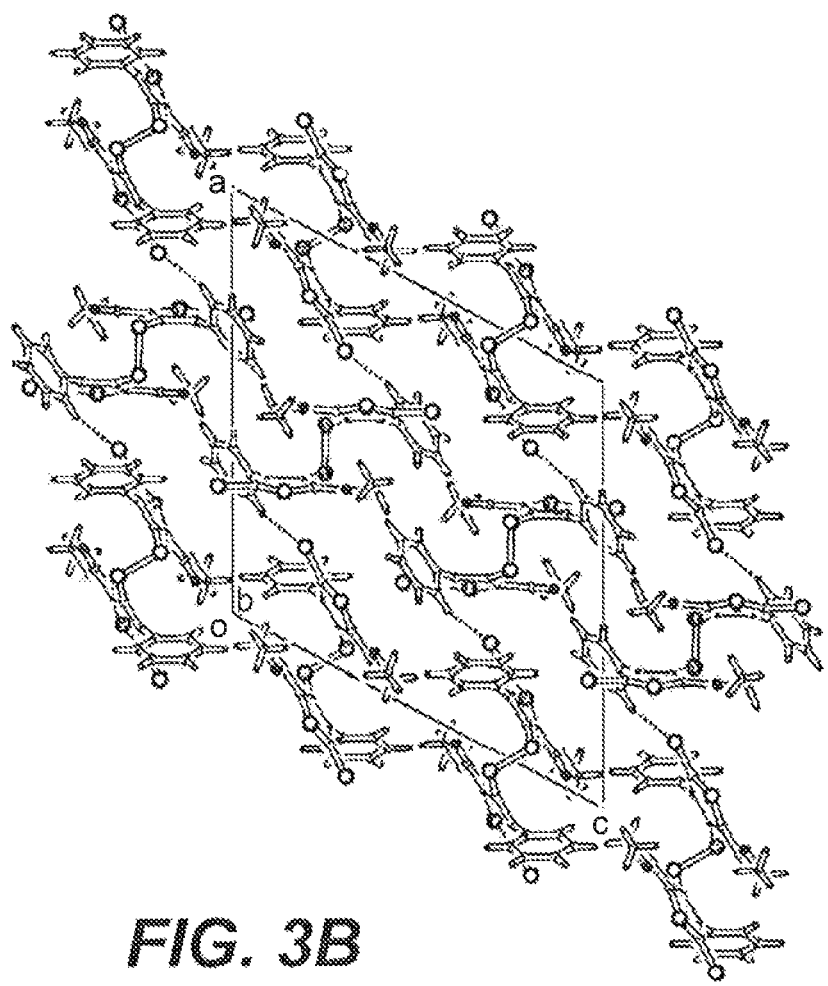
FIG. 3B depicts a packing diagram of compound 6 with projection along the crystallographic b-axis.

In the molecules, the ethyl ester group A (C1/C2/C3/O1/O2) and the 1,3-dithiolane-2-thione ring B (C4-C6/S1-S3) are planar, with rms deviations of 0.0230 Å and 0.0070 Å, respectively. The ethanethiol group C (S4/C7/C8) is planar. The dihedral angles between A/B, A/C and B/C are 4.73 (10)°, 7.58 (14)° and 3.47 (11)°, respectively. The molecules are stabilized in the form of dimmer due to C—H . . . O bond as shown in FIG. 3A.

Compound 6, diethyl 4,4'-disulfanediylbis(3-phenyl-2-thioxo-2,3-dihydrothiazole-5-carboxylate), may take the form of two conformers with center of symmetry. One conformer consists of disordered molecules with disorder in ethyl ester groups. In non-disordered molecules, referring to groups A-F in FIG. 2A, the ethyl ester group A (C1-C3/O1/O2), the 4-sulfanyl-1,3-thiazole-2(3H)-thione group B (C4-C6/S1/S2/S3) and the phenyl group C (C7-C12) are planar with root-mean-square (rms) deviation of 0.0820, 0.0154 and 0.0074 Å, respectively. The dihedral angles between A/B, A/C and B/C is 16.55 (4)°, 56.82 (15)° and 66.07 (7)°, respectively. In disordered molecules, the ethyl ester groups D (C13A-C14A/O3A/C15/O4) and E (C13B-C14B/O3B/C15/O4) have an occupancy ratio of 0.651(6):0.349(6) and a rms deviation of 0.0578:0.3947, the 4-sulfanyl-1,3-thiazole-2(3H)-thione group F (C16-C18/S4/S5/S6) and the phenyl group G (C19-C24) are planar with rms deviation of 0.0079 and 0.0057 Å, respectively. The dihedral angle between D/F, D/G, E/F, E/G and F/G is 13.72(1.02)°, 56.9 (4)°, 13.3 (3.9)°, 57.27 (1.55)° and 70.58 (7)°, respectively. Additional information relating to compound 6 is provided in Tables 2-7 below. Table 2 shows crystal data and structure refinement for compound 6. Table 3 shows atomic coordinates (×10$^4$) and equivalent isotropic displacement parameters (Å2×10$^3$) for compound 6. U(eq) is defined as one third of the trace of the orthogonalized Uij tensor. Table 4 shows bond lengths [Å] for compound 6. Table 5 shows angles [°] for compound 6. Table 6 shows anisotropic displacement parameters (Å2×10) for compound 6. The anisotropic displacement factor exponent takes the form: $-2\pi^2[h^2a^{*2}U^{11} + \ldots + 2 h k a^*b^*U^{12}]$. Table 7 shows torsion angles [°] for compound 6. The symmetry transformations used to generate equivalent atoms were: i=−x+1,y,−z+½ ii=−x,y,−z+½.

TABLE 2

| | | | |
|---|---|---|---|
| Empirical formula | $C_{48}H_4N_4O_8S_{12}$ | | |
| Formula weight | 1185.56 | | |
| Temperature | 296(2) K | | |
| Wavelength | 0.71073 Å | | |
| Crystal system | Monoclinic | | |
| Space group | P2/c | | |
| Unit cell dimensions | a = 18.3444(7) Å | α = 90° | |
| | b = 9.3026(4) Å | β = 117.9380(10)° | |
| | c = 18.0149(6) Å | γ = 90° | |
| Volume | 2715.96(18) Å$^3$ | | |
| Z | 2 | | |
| Density (calculated) | 1.450 Mg/m$^3$ | | |
| Absorption coefficient | 0.538 mm$^{-1}$ | | |
| F(000) | 1224 | | |
| Crystal size | 0.450 × 0.400 × 0.380 mm$^3$ | | |
| Theta range for data collection | 2.189 to 27.899° | | |
| Index ranges | −24 <= h <= 24, −12 <= k <= 11, −23 <= l <= 18 | | |
| Reflections collected | 18749 | | |
| Independent reflections | 6451 [R(int) = 0.0376] | | |
| Completeness to theta = 25.242° | 99.7% | | |
| Refinement method | Full-matrix least-squares on F$^2$ | | |
| Data/restraints/parameters | 6451/4/326 | | |
| Goodness-of-fit on F | 1.015 | | |
| Final R indices [I > 2sigma(I)] | R1 = 0.0458, wR2 = 0.1145 | | |
| R indices (all data) | R1 = 0.0693, wR2 = 0.1307 | | |
| Extinction coefficient | n/a | | |
| Largest diff. peak and hole | 0.355 and −0.257 e.Å$^{-3}$ | | |

TABLE 3

| | x | y | z | U(eq) |
|---|---|---|---|---|
| S(1) | 4424(1) | 593(1) | 2478(1) | 49(1) |
| S(2) | 2818(1) | 3828(1) | −390(1) | 79(1) |
| S(3) | 3495(1) | 4695(1) | 1393(1) | 54(1) |
| O(1) | 4319(2) | 5309(2) | 3092(1) | 76(1) |
| O(2) | 4548(2) | 3144(2) | 3678(1) | 77(1) |
| N(1) | 3585(1) | 2112(2) | 985(1) | 46(1) |
| C(1) | 4771(3) | 7535(4) | 3738(3) | 104(1) |
| C(2) | 4662(2) | 6042(3) | 3910(2) | 83(1) |
| C(3) | 4309(2) | 3894(3) | 3075(2) | 51(1) |
| C(4) | 3965(1) | 3440(2) | 2182(1) | 45(1) |
| C(5) | 3968(1) | 2118(2) | 1869(1) | 43(1) |
| C(6) | 3295(1) | 3431(3) | 621(2) | 51(1) |
| C(7) | 3490(1) | 842(3) | 488(1) | 48(1) |
| C(8) | 3897(2) | 764(3) | 10(2) | 58(1) |
| C(9) | 3794(2) | −434(3) | −479(2) | 69(1) |
| C(10) | 3309(2) | −1547(3) | −471(2) | 74(1) |
| C(11) | 2909(2) | −1468(3) | 7(2) | 76(1) |
| C(12) | 2988(2) | −255(3) | 488(2) | 63(1) |
| S(4) | 538(1) | 5267(1) | 3066(1) | 56(1) |
| S(5) | 2448(1) | 8131(1) | 1959(1) | 87(1) |
| S(6) | 1618(1) | 9235(1) | 2918(1) | 66(1) |
| O(4) | 304(1) | 7937(3) | 3993(1) | 82(1) |
| N(2) | 1495(1) | 6625(2) | 2472(1) | 47(1) |
| O(3A) | 638(7) | 10094(9) | 3653(9) | 105(2) |
| C(13A) | 501(4) | 12239(6) | 4199(5) | 105(2) |
| C(14A) | 417(5) | 10679(7) | 4287(6) | 105(2) |
| O(3B) | 791(14) | 9961(17) | 3821(17) | 105(2) |
| C(13B) | 642(7) | 11497(14) | 4709(8) | 105(2) |
| C(14B) | 85(9) | 11075(14) | 3855(9) | 105(2) |
| C(15) | 639(2) | 8623(3) | 3685(2) | 65(1) |
| C(16) | 1043(1) | 8082(3) | 3193(2) | 52(1) |
| C(17) | 1044(1) | 6743(3) | 2917(1) | 46(1) |
| C(18) | 1858(2) | 7880(3) | 2414(2) | 56(1) |
| C(19) | 1563(1) | 5318(3) | 2075(2) | 49(1) |
| C(20) | 2034(2) | 4193(3) | 2555(2) | 60(1) |
| C(21) | 2093(2) | 2954(3) | 2161(2) | 74(1) |
| C(22) | 1698(2) | 2873(4) | 1300(2) | 82(1) |
| C(23) | 1238(2) | 4009(4) | 828(2) | 80(1) |
| C(24) | 1158(2) | 5243(3) | 1209(2) | 65(1) |

TABLE 4

| | |
|---|---|
| S(1)-C(5) | 1.749(2) |
| S(1)-S(1)$^i$ | 2.0773(12) |
| S(2)-C(6) | 1.651(2) |
| S(3)-C(6) | 1.723(3) |

TABLE 4-continued

| | |
|---|---|
| S(3)-C(4) | 1.727(2) |
| O(1)-C(3) | 1.316(3) |
| O(1)-C(2) | 1.471(3) |
| O(2)-C(3) | 1.188(3) |
| N(1)-C(6) | 1.376(3) |
| N(1)-C(5) | 1.408(3) |
| N(1)-C(7) | 1.442(3) |
| C(1)-C(2) | 1.457(5) |
| C(1)-H(1A) | 0.9600 |
| C(1)-H(1B) | 0.9600 |
| C(1)-H(1C) | 0.9600 |
| C(2)-H(2A) | 0.9700 |
| C(2)-H(2B) | 0.9700 |
| C(3)-C(4) | 1.488(3) |
| C(4)-C(5) | 1.354(3) |
| C(7)-C(12) | 1.375(3) |
| C(7)-C(8) | 1.382(3) |
| C(8)-C(9) | 1.378(4) |
| C(8)-H(8) | 0.9300 |
| C(9)-C(10) | 1.369(4) |
| C(9)-H(9) | 0.9300 |
| C(10)-C(11) | 1.371(4) |
| C(10)-H(10) | 0.9300 |
| C(11)-C(12) | 1.387(4) |
| C(11)-H(11) | 0.9300 |
| C(12)-H(12) | 0.9300 |
| S(4)-C(17) | 1.746(2) |
| S(4)-S(4)$^{ii}$ | 2.0696(13) |
| S(5)-C(18) | 1.651(3) |
| S(6)-C(18) | 1.727(3) |
| S(6)-C(16) | 1.732(2) |
| O(4)-C(15) | 1.187(3) |
| N(2)-C(18) | 1.372(3) |
| N(2)-C(17) | 1.401(3) |
| N(2)-C(19) | 1.445(3) |
| O(3A)-C(15) | 1.370(9) |
| O(3A)-C(14A) | 1.483(17) |
| C(13A)-C(14A) | 1.476(9) |
| C(13A)-H(13A) | 0.9600 |
| C(13A)-H(13B) | 0.9600 |
| C(13A)-H(13C) | 0.9600 |
| C(14A)-H(14A) | 0.9700 |
| C(14A)-H(14B) | 0.9700 |
| O(3B)-C(15) | 1.274(16) |
| O(3B)-C(14B) | 1.68(3) |
| C(13B)-C(14B) | 1.446(15) |
| C(13B)-H(13D) | 0.9600 |
| C(13B)-H(13E) | 0.9600 |
| C(13B)-H(13F) | 0.9600 |
| C(14B)-H(14C) | 0.9700 |
| C(14B)-H(14D) | 0.9700 |
| C(15)-C(16) | 1.485(4) |
| C(16)-C(17) | 1.342(3) |
| C(19)-C(20) | 1.375(4) |
| C(19)-C(24) | 1.380(4) |
| C(20)-C(21) | 1.384(4) |
| C(20)-H(20) | 0.9300 |
| C(21)-C(22) | 1.374(5) |
| C(21)-H(21) | 0.9300 |
| C(22)-C(23) | 1.371(5) |
| C(22)-H(22) | 0.9300 |
| C(23)-C(24) | 1.380(4) |
| C(23)-H(23) | 0.9300 |
| C(24)-H(24) | 0.9300 |

TABLE 5

| | |
|---|---|
| C(5)-S(1)-S(1)$^{i}$ | 101.69(7) |
| C(6)-S(3)-C(4) | 92.21(11) |
| C(3)-O(1)-C(2) | 118.7(2) |
| C(6)-N(1)-C(5) | 114.32(19) |
| C(6)-N(1)-C(7) | 121.85(18) |
| C(5)-N(1)-C(7) | 123.82(19) |
| C(2)-C(1)-H(1A) | 109.5 |
| C(2)-C(1)-H(1B) | 109.5 |
| H(1A)-C(1)-H(1B) | 109.5 |
| C(2)-C(1)-H(1C) | 109.5 |

TABLE 5-continued

| | |
|---|---|
| H(1A)-C(1)-H(1C) | 109.5 |
| H(1B)-C(1)-H(1C) | 109.5 |
| C(1)-C(2)-O(1) | 105.4(3) |
| C(1)-C(2)-H(2A) | 110.7 |
| O(1)-C(2)-H(2A) | 110.7 |
| C(1)-C(2)-H(2B) | 110.7 |
| O(1)-C(2)-H(2B) | 110.7 |
| H(2A)-C(2)-H(2B) | 108.8 |
| O(2)-C(3)-O(1) | 124.9(2) |
| O(2)-C(3)-C(4) | 127.5(2) |
| O(1)-C(3)-C(4) | 107.6(2) |
| C(5)-C(4)-C(3) | 128.8(2) |
| C(5)-C(4)-S(3) | 111.62(16) |
| C(3)-C(4)-S(3) | 119.61(18) |
| C(4)-C(5)-N(1) | 112.22(19) |
| C(4)-C(5)-S(1) | 124.72(17) |
| N(1)-C(5)-S(1) | 123.03(17) |
| N(1)-C(6)-S(2) | 127.73(19) |
| N(1)-C(6)-S(3) | 109.62(16) |
| S(2)-C(6)-S(3) | 122.64(15) |
| C(12)-C(7)-C(8) | 121.2(2) |
| C(12)-C(7)-N(1) | 119.7(2) |
| C(8)-C(7)-N(1) | 119.1(2) |
| C(9)-C(8)-C(7) | 119.2(3) |
| C(9)-C(8)-H(8) | 120.4 |
| C(7)-C(8)-H(8) | 120.4 |
| C(10)-C(9)-C(8) | 120.0(3) |
| C(10)-C(9)-H(9) | 120.0 |
| C(8)-C(9)-H(9) | 120.0 |
| C(9)-C(10)-C(11) | 120.6(3) |
| C(9)-C(10)-H(10) | 119.7 |
| C(11)C(10)-H(10) | 119.7 |
| C(10)-C(11)-C(12) | 120.3(3) |
| C(10)-C(11)-H(11) | 119.9 |
| C(12)-C(11)-H(11) | 119.9 |
| C(7)-C(12)-C(11) | 118.6(3) |
| C(7)-C(12)-H(12) | 120.7 |
| C(11)-C(12)-H(12) | 120.7 |
| C(17)-S(4)-S(4)$^{ii}$ | 100.31(8) |
| C(18)-S(6)-C(16) | 92.19(12) |
| C(18)-N(2)-C(17) | 114.5(2) |
| C(18)-N(2)-C(19) | 121.42(19) |
| C(17)-N(2)-C(19) | 124.03(19) |
| C(15)-O(3A)-C(14A) | 109.2(10) |
| C(14A)-C(13A)-H(13A) | 109.5 |
| C(14A)-C(13A)-H(13B) | 109.5 |
| H(13A)-C(13A)-H(13B) | 109.5 |
| C(14A)-C(13A)-H(13C) | 109.5 |
| H(13A)-C(13A)-H(13C) | 109.5 |
| H(13B)-C(13A)-H(13C) | 109.5 |
| C(13A)-C(14A)-O(3A) | 101.4(7) |
| C(13A)-C(14A)-H(14A) | 111.5 |
| O(3A)-C(14A)-H(14A) | 111.5 |
| C(13A)-C(14A)-H(14B) | 111.5 |
| O(3A)-C(14A)-H(14B) | 111.5 |
| H(14A)-C(14A)-H(14B) | 109.3 |
| C(15)-O(3B)-C(14B) | 120.3(17) |
| C(14B)-C(13B)-H(13D) | 109.5 |
| C(14B)-C(13B)-H(13E) | 109.5 |
| H(13D)-C(13B)-H(13E) | 109.5 |
| C(14B)-C(13B)-H(13F) | 109.5 |
| H(13D)-C(13B)-H(13F) | 109.5 |
| H(13E)-C(13B)-H(13F) | 109.5 |
| C(13B)-C(14B)-O(3B) | 91.9(13) |
| C(13B)-C(14B)-H(14C) | 113.3 |
| O(3B)-C(14B)-H(14C) | 113.3 |
| C(13B)-C(14B)-H(14D) | 113.3 |
| O(3B)-C(14B)-H(14D) | 113.3 |
| H(14C)-C(14B)-H(14D) | 110.6 |
| O(4)-C(15)-O(3B) | 123.4(13) |
| O(4)-C(15)-O(3A) | 124.5(6) |
| O(4)-C(15)-C(16) | 127.5(3) |
| O(3B)-C(15)-C(16) | 108.6(12) |
| O(3A)-C(15)-C(16) | 107.7(6) |
| C(17)-C(16)-C(15) | 128.5(2) |
| C(17)-C(16)-S(6) | 111.25(18) |
| C(15)-C(16)-S(6) | 120.2(2) |
| C(16)-C(17)-N(2) | 112.8(2) |
| C(16)-C(17)-S(4) | 125.47(18) |
| N(2)-C(17)-S(4) | 121.70(18) |

TABLE 5-continued

| | |
|---|---|
| N(2)-C(18)-S(5) | 127.7(2) |
| N(2)-C(18)-S(6) | 109.19(17) |
| S(5)-C(18)-S(6) | 123.07(16) |
| C(20)-C(19)-C(24) | 121.3(3) |
| C(20)-C(19)-N(2) | 120.3(2) |
| C(24)-C(19)-N(2) | 118.4(2) |
| C(19)-C(20)-C(21) | 119.3(3) |
| C(19)-C(20)-H(20) | 120.4 |
| C(21)-C(20)-H(20) | 120.4 |
| C(22)-C(21)-C(20) | 119.9(3) |
| C(22)-C(21)-H(21) | 120.1 |
| C(20)-C(21)-H(21) | 120.1 |
| C(23)-C(22)-C(21) | 120.2(3) |
| C(23)-C(22)-H(22) | 119.9 |
| C(21)-C(22)-H(22) | 119.9 |
| C(22)-C(23)-C(24) | 120.7(3) |
| C(22)-C(23)-H(23) | 119.6 |
| C(24)-C(23)-H(23) | 119.6 |
| C(19)-C(24)-C(23) | 118.6(3) |
| C(19)-C(24)-H(24) | 120.7 |
| C(23)-C(24)-H(24) | 120.7 |

TABLE 6

| | $U^{11}$ | $U^{22}$ | $U^{33}$ | $U^{23}$ | $U^{13}$ | $U^{12}$ |
|---|---|---|---|---|---|---|
| S(1) | 53(1) | 45(1) | 47(1) | 6(1) | 23(1) | −3(1) |
| S(2) | 89(1) | 73(1) | 42(1) | 6(1) | 3(1) | 7(1) |
| S(3) | 56(1) | 46(1) | 49(1) | 2(1) | 15(1) | 4(1) |
| O(1) | 117(2) | 51(1) | 47(1) | −6(1) | 28(1) | 3(1) |
| O(2) | 118(2) | 61(1) | 48(1) | 5(1) | 35(1) | 4(1) |
| N(1) | 44(1) | 49(1) | 39(1) | 0(1) | 15(1) | −3(1) |
| C(1) | 117(3) | 78(2) | 103(3) | −25(2) | 41(2) | −13(2) |
| C(2) | 120(3) | 68(2) | 55(2) | −14(2) | 38(2) | 5(2) |
| C(3) | 55(1) | 50(1) | 48(1) | −2(1) | 25(1) | 1(1) |
| C(4) | 43(1) | 49(1) | 42(1) | −2(1) | 17(1) | 0(1) |
| C(5) | 41(1) | 46(1) | 41(1) | 1(1) | 18(1) | −2(1) |
| C(6) | 45(1) | 52(1) | 45(1) | 3(1) | 11(1) | −2(1) |
| C(7) | 45(1) | 51(1) | 41(1) | −3(1) | 14(1) | −3(1) |
| C(8) | 6191 | 60(2) | 54(1) | −4(1) | 28(1) | −4(1) |
| C(9) | 76(2) | 75(2) | 55(2) | −8(1) | 31(1) | 6(2) |
| C(10) | 76(2) | 66(2) | 62(2) | −21(1) | 17(2) | 0(2) |
| C(11) | 71(2) | 61(2) | 84(2) | −13(2) | 24(2) | −20(1) |
| C(12) | 59(2) | 64(2) | 66(2) | −10(1) | 29(1) | −14(1) |
| S(4) | 54(1) | 61(1) | 62(1) | 15(1) | 34(1) | 6(1) |
| S(5) | 92(1) | 91(1) | 113(1) | −2(1) | 77(1) | −15(1) |
| S(6) | 66(1) | 60(1) | 83(1) | −9(1) | 44(1) | −11(1) |
| O(4) | 96(2) | 93(2) | 80(1) | −7(1) | 62(1) | −6(1) |
| N(2) | 41(1) | 56(1) | 46(1) | 3(1) | 22(1) | 2(1) |
| O(3A) | 133(3) | 74(2) | 159(5) | −34(2) | 112(4) | −15(2) |
| C(13A) | 133(3) | 74(2) | 159(5) | −34(2) | 112(4) | −15(2) |
| C(14A) | 133(3) | 74(2) | 159(5) | −34(2) | 112(4) | −15(2) |
| O(3B) | 133(3) | 74(2) | 159(5) | −34(2) | 112(4) | −15(2) |
| C(13B) | 133(3) | 74(2) | 159(5) | −34(2) | 112(4) | −15(2) |
| C(14B) | 133(3) | 74(2) | 159(5) | −34(2) | 112(4) | −15(2) |
| C(15) | 60(2) | 78(2) | 60(2) | −14(1) | 31(1) | −6(2) |
| C(16) | 46(1) | 64(2) | 49(1) | 0(1) | 23(1) | 0(1) |
| C(17) | 38(1) | 59(1) | 40(1) | 5(1) | 18(1) | 2(1) |
| C(18) | 51(1) | 63(2) | 59(2) | 2(1) | 30(1) | −4(1) |
| C(19) | 41(1) | 61(1) | 49(1) | −1(1) | 24(1) | −1(1) |
| C(20) | 56(1) | 64(2) | 59(2) | 1(1) | 27(1) | 5(1) |
| C(21) | 70(2) | 65(2) | 97(2) | −4(2) | 47(2) | 5(1) |
| C(22) | 74(2) | 83(2) | 107(3) | −37(2) | 58(2) | −16(2) |
| C(23) | 72(2) | 107(3) | 63(2) | −28(2) | 35(2) | −14(2) |
| C(24) | 54(1) | 85(2) | 53(2) | −2(1) | 23(1) | 2(1) |

TABLE 7

| | |
|---|---|
| C(3)-O(1)-C(2)-C(1) | 166.7(3) |
| C(2)-O(1)-C(3)-O(2) | 1.0(4) |
| C(2)-O(1)-C(3)-C(4) | −177.8(2) |
| O(2)-C(3)-C(4)-C(5) | −11.5(4) |
| O(1)-C(3)-C(4)-C(5) | 167.3(2) |
| O(2)-C(3)-C(4)-S(3) | 169.2(2) |
| O(1)-C(3)-C(4)-S(3) | −12.0(3) |

TABLE 7-continued

| | |
|---|---|
| C(6)-S(3)-C(4)-C(5) | −0.01(18) |
| C(6)-S(3)-C(4)-C(3) | 179.46(19) |
| C(3)-C(4)-C(5)-N(1) | −179.7(2) |
| S(3)-C(4)-C(5)-N(1) | −0.3(2) |
| C(3)-C(4)-C(5)-S(1) | −1.9(4) |
| S(3)-C(4)-C(5)-S(1) | 177.48(12) |
| C(6)-N(1)-C(5)-C(4) | 0.5(3) |
| C(7)-N(1)-C(5)-C(4) | −178.9(2) |
| C(6)-N(1)-C(5)-S(1) | −177.29(16) |
| C(7)-N(1)-C(5)-S(1) | 3.3(3) |
| S(1)$^i$-S(1)-C(5)-C(4) | −95.09(19) |
| S(1)$^i$-S(1)-C(5)-N(1) | 82.43(17) |
| C(5)-N(1)-C(6)-S(2) | 179.86(18) |
| C(7)-N(1)-C(6)-S(2) | −0.7(3) |
| C(5)-N(1)-C(6)-S(3) | −0.5(2) |
| C(7)-N(1)-C(6)-S(3) | 178.91(16) |
| C(4)-S(3)-C(6)-N(1) | 0.29(18) |
| C(4)-S(3)-C(6)-S(2) | 179.95(17) |
| C(6)-N(1)-C(7)-C(12) | −113.3(3) |
| C(5)-N(1)-C(7)-C(12) | 66.1(3) |
| C(6)-N(1)-C(7)-C(8) | 65.7(3) |
| C(5)-N(1)-C(7)-C(8) | −114.9(2) |
| C(12)-C(7)-C(8)-C(9) | 0.3(4) |
| N(1)-C(7)-C(8)-C(9) | −178.7(2) |
| C(7)-C(8)-C(9)-C(10) | −1.7(4) |
| C(8)-C(9)-C(10)-C(11) | 1.4(5) |
| C(9)-C(10)-C(11)-C(12) | 0.2(5) |
| C(8)-C(7)-C(12)-C(11) | 1.3(4) |
| N(1)-C(7)-C(12)-C(11) | −179.8(2) |
| C(10)-C(11)-C(12)-C(7) | −1.6(4) |
| C(15)-O(3A)-C(14A)-C(13A) | 176.5(7) |
| C(15)-O(3B)-C(14B)-C(13B) | 120(2) |
| C(14B)-O(3B)-C(15)-O(4) | −42(3) |
| C(14B)-O(3B)-C(15)-C(16) | 146.0(17) |
| C(14A)-O(3A)-C(15)-O(4) | 18.8(12) |
| C(14A)-O(3A)-C(15)-C(16) | −167.2(7) |
| O(4)-C(15)-C(16)-C(17) | 7.8(5) |
| O(3B)-C(15)-C(16)-C(17) | 179.8(12) |
| O(3A)-C(15)-C(16)-C(17) | −165.9(6) |
| O(4)-C(15)-C(16)-S(6) | −171.2(2) |
| O(3B)-C(15)-C(16)-S(6) | 0.8(12) |
| O(3A)-C(15)-C(16)-S(6) | 15.0(6) |
| C(18)-S(6)-C(16)-C(17) | 0.4(2) |
| C(18)-S(6)-C(16)-C(15) | 179.5(2) |
| C(15)-C(16)-C(17)-N(2) | −179.9(2) |
| S(6)-C(16)-C(17)-N(2) | −0.8(3) |
| C(15)-C(16)-C(17)-S(4) | 0.8(4) |
| S(6)-C(16)-C(17)-S(4) | 179.92(13) |
| C(18)-N(2)-C(17)-C(16) | 1.0(3) |
| C(19)-N(2)-C(17)-C(16) | −177.1(2) |
| C(18)-N(2)-C(17)-S(4) | −179.72(17) |
| C(19)-N(2)-C(17)-S(4) | 2.2(3) |
| S(4)$^{ii}$-S(4)-C(17)-C(16) | 96.9(2) |
| S(4)$^{ii}$-S(4)-C(17)-N(2) | −82.38(17) |
| C(17)-N(2)-C(18)-S(5) | 178.46(17) |
| C(19)-N(2)-C(18)-S(5) | −3.4(3) |
| C(17)-N(2)-C(18)-S(6) | −0.6(3) |
| C(19)-N(2)-C(18)-S(6) | 177.47(16) |
| C(16)-S(6)-C(18)-N(2) | 0.17(19) |
| C(16)-S(6)-C(18)-S(5) | −178.99(18) |
| C(18)-N(2)-C(19)-C(20) | 109.7(3) |
| C(17)-N(2)-C(19)-C(20) | −72.4(3) |
| C(18)-N(2)-C(19)-C(24) | −69.1(3) |
| C(17)-N(2)-C(19)-C(24) | 108.8(3) |
| C(24)-C(19)-C(20)-C(21) | −1.0(4) |
| N(2)-C(19)-C(20)-C(21) | −179.8(2) |
| C(19)-C(20)-C(21)-C(22) | 1.6(4) |
| C(20)-C(21)-C(22)-C(23) | −0.8(5) |
| C(21)-C(22)-C(23)-C(24) | −0.5(5) |
| C(20)-C(19)-C(24)-C(23) | −0.3(4) |
| N(2)-C(19)-C(24)-C(23) | 178.5(2) |
| C(22)-C(23)-C(24)-C(19) | 1.0(4) |

Figure 4:
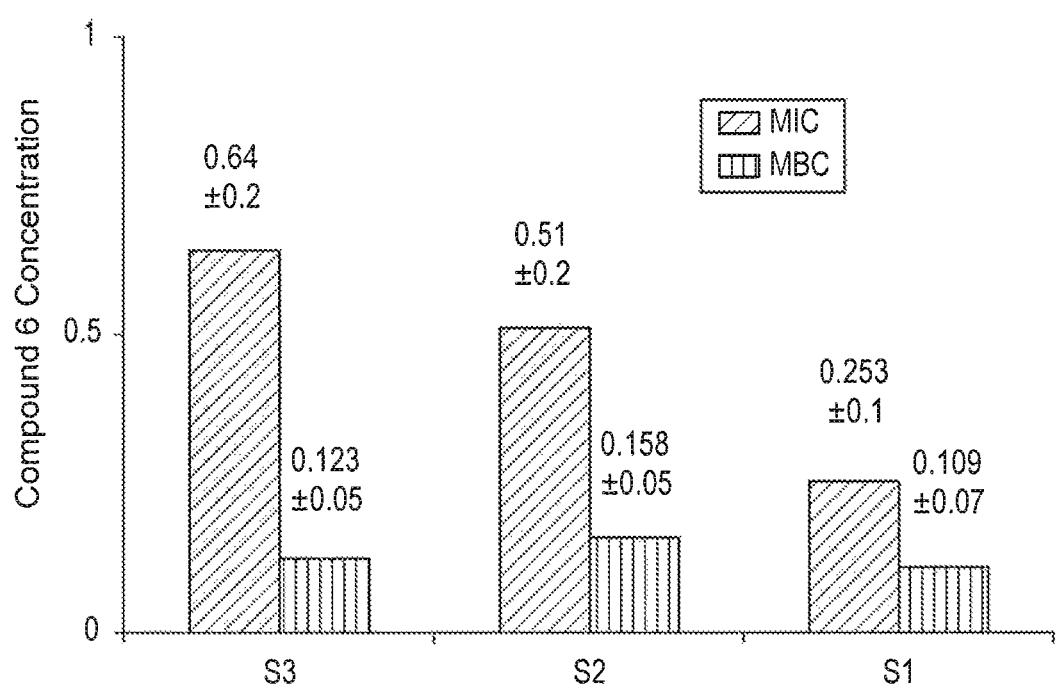
FIG. 4 is a graph depicting the mean±standard deviation of the minimal inhibitory concentration (MIC) and minimal bactericidal concentration (MBC) of the exemplary synthesized compound 6 (S1, S2 and S3 correspond to S. epidermidis S1, S. epidermidis S2 and S. epidermidis S3, respectively.)

As shown in FIG. 4, Compound 6 demonstrated antimicrobial activity against three strains of *S. epidermidis*. Compound 6 showed strongest antimicrobial activity against *S. epidermidis* (S1), which was also susceptible to all tested antibiotics except for erythromycin. Compound 6 was also effective as an antimicrobial against multi-antibiotics resistant *S. epidermidis* S2 and *S. epidermidis* S3. Consistent with these results, compound 6 may be effective as a novel antimicrobial agent for multidrug resistant pathogenic bacteria. Table 8 shows susceptibility of three bacterial strains of *S. epidermidis* to standard antibiotics.

TABLE 8

| Antibiotics | S. epidermidis S1 | S. epidermidis S2 | S. epidermidis S3 |
|---|---|---|---|
| Amox/K Clav | S | R | R |
| Ciprofloxacin | S | R | R |
| Clindamycin | S | R | R |
| Daptomycin | S | R | R |

TABLE 8-continued

| Antibiotics | S. epidermidis S1 | S. epidermidis S2 | S. epidermidis S3 |
|---|---|---|---|
| Erythromycin | R | R | R |
| Fosfomycin | S | S | S |
| Fusidic Acid | S | R | R |
| Gentamicin | S | S | S |
| Lmipenem | S | S | S |
| Levofloxacin | S | R | S |
| Linezolid | S | R | R |
| Moxifloxacin | S | R | S |
| Mupirocin | S | R | R |
| Oxacillin | S | R | R |
| Rifampin | S | R | R |
| Synercid | S | R | R |
| Teicoplanin | S | R | S |
| Tetracycline | S | S | S |
| Trimethoprim/Sulfamethoxazole | S | R | S |
| Vancomycin | S | R | S |

S = susceptible, R = Resistant, I = intermediate.

Figure 5A:
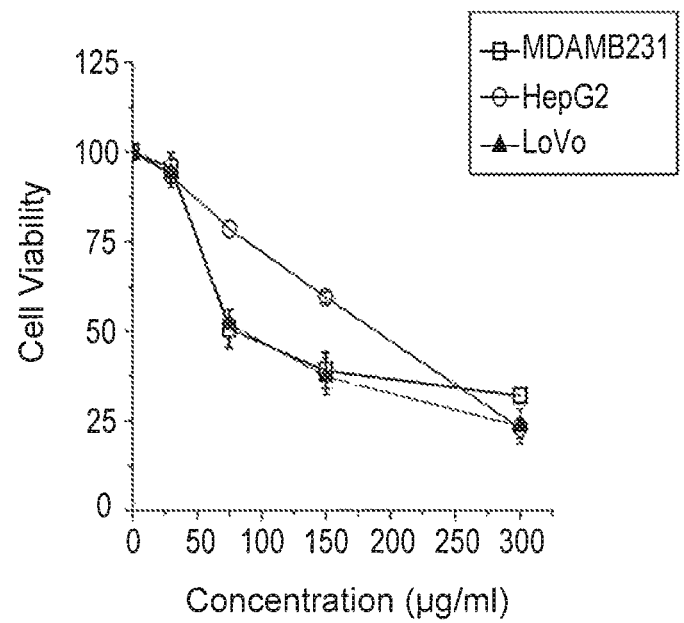
FIG. 5A is a graph depicting cytotoxic effects of compound 6 on HepG2, LoVo and MBA-MD-231 cancer cells treated for 48 hours with different concentrations of compound 6, determined by an MTT assay (percentage of treated cells relative to untreated control are expressed as the mean±standard deviation of three independent experiments)

Compound 6 further demonstrated anti-cancer activity, as shown in Table 9 and FIG. 5A. Breast cancer cell-line MDA-MB-231 and colon cancer cell line LoVo were more sensitive to compound 6 than liver cancer cell line HepG2, according to the $IC_{50}$ values reported in Table 8. Table 9 depicts anti-cancer activity of compound 6.

TABLE 9

| Cell line Type | $IC_{50}$ (µg/ml) |
|---|---|
| MDA-MB-231 (Breast cancer) | 75 |
| HepG2 (Liver cancer) | 190 |
| LoVo (Colon cancer) | 75 |

Figure 5B:
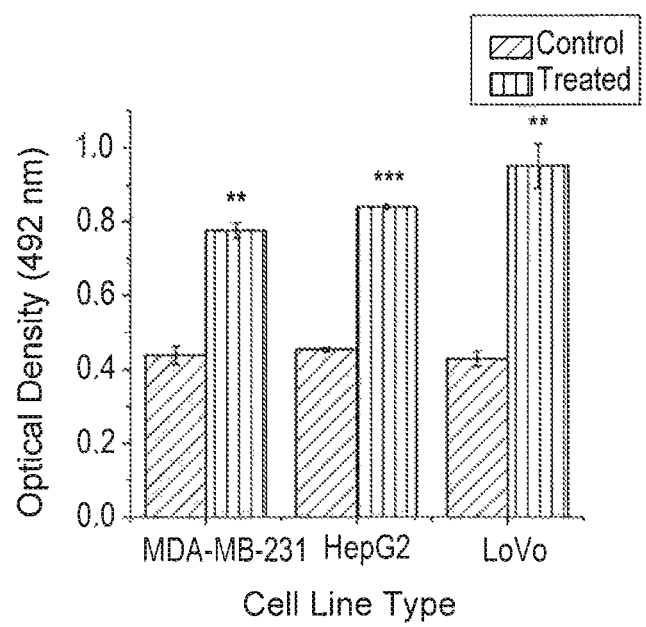
FIG. 5B is a graph depicting lactate dehydrogenase (LDH) activity determined for cells treated at 492 nm in an ELISA plate reader (values represent the means±standard deviation of three independent experiments (*P<0.05, P<0.01, *P<0.001 indicate significance of difference compared to control)).

Cytotoxicity of compound 6 was further demonstrated by measuring lactate dehydrogenase (LDH) release levels for cancer cells grown in cell culture medium (FIG. 5B). LDH release was significantly induced in each of the three different cancer cell types by compound 6, indicative of cell membrane damage. Compound 6 more effectively sensitizes adenocarcinoma cells (MDA-MB-231 and LoVo cells) than HepG2 cells, suggesting that compound 6 may target specific cell pathways.

Compound 6 is a promising larvicidal agent in addition to an effective anticancer and anti-antibiotic resistant bacteria agent. Toxic activities of compound 6 were assessed against 3rd larval instars of the Filaria vector, Cx. *pipiens*. All tested concentrations resulted in mortality of Cx. *pipiens* at 72 h against 4th instars. However, susceptibility of mosquito larvae positively correlated with compound 6 concentration and period of exposure. In particular, median lethal dose ($LD_{50}$) value for compound 6 was measured to be 142.73, 119.68 and 102.18 µg/mL after 24, 48 and 72 h, respectively. Table 10 shows mosquito larvicidal activity of compound 6 against 4th instar larvae of Cx. *pipiens*.

TABLE 10

| Species | | (%) Mortality Concentration (µg/ml) | | | | $LD_{50}$ | $LD_{90}$ |
|---|---|---|---|---|---|---|---|
| Mosquito | Time | 75 | 100 | 150 | 200 | (µg/ml) | (µg/ml) |
| Cx. pipiens | 24 | 0 ± 00 | 33.33 ± 3.33 | 46.67 ± 2.16 | 90 ± 5.77 | 142.73 | 204.01 |
| | 48 | 13.33 ± 4.71 | 46.67 ± 2.16 | 70 ± 3.33 | 100 ± 00 | 119.68 | 181.36 |
| | 72 | 23.33 ± 2.05 | 63.33 ± 6.67 | 76.67 ± 3.33 | 100 ± 00 | 102.18 | 175.63 |

The present teachings will be understood more readily by reference to the following examples, which are provided by way of illustration.

EXAMPLES

Example 1

Synthesis of diethyl 4,4'-disulfanediylbis(3-phenyl-2-thioxo-2,3-dihydrothiazole-5-carboxylate) (6)

A mixture of diethyl 2,2'-thiocarbonylbis(sulfanediyl)diacetate 1 (2.82 g, 10 mmol), phenyl isothiocyanate 2 (2.70 g, 20 mmol) and anhydrous $K_2CO_3$ (10 g) in DMF (30 ml) was stirred at room temperature for 12 hours. The reaction mixture was poured into 5 ml HCl/50 ml $H_2O$ mixture. The crude solid product that formed was filtered off, washed with water/ethanol mixture (ethanol dissolved any residual compound 5, but not compound 6) and dried, resulting in a final sample including compound 6. Recrystallization in DMF afforded yellow crystals of compound 6, yield 40%; m.p. 225° C., IR (KBr, cm$^{-1}$) v=3057 (aromatic CH), 2981 (aliphatic CH), 1722 (C=O); $^1$H-NMR (500 MHz, CDCl$_3$)=1.36 (t, 611, OCH$_2$-C$\underline{H}_3$, J=7 Hz), 4.33 (q, 7, 4H, OC$\underline{H}_2$—CH$_3$ J=7 Hz), 7.25-7.51 (m, 10H, Ar—H); $^{13}$C-NMR (125 MHz, CDCl$_3$)=14.30, 62.86, 125.3, 129.00, 129.58, 130.13, 137.12, 138.27, 157.60, 189.55. Anal. calcd for $C_{24}H_{20}N_2O_4S_6$: C, 48.62; 11, 3.40; N, 4.73. Found: C, 48.55; H, 3.35; N, 4.82.

Example 2

Antimicrobial Test

Compound 6, synthesized as above, was evaluated as an antimicrobial agent against selected antibiotics resistant *Staphylococcus epidermidis*. The bacterial strains were obtained from Laboratory (2b56) of the Botany and Microbiology Department, College of Science, King Saud University, Riyadh. The bacterial strains were isolated from the skin of healthy students and identified by an automated antibiotic susceptibility testing system, Vitek System (BioMerieux, France). Two strains were determined to be multi-resistance bacteria, while the other was determined to be a susceptible strain based on susceptibility testing using the Vitek System (Table 2). The minimal inhibitory concentration (MIC) and minimal bactericidal concentration (MBC) of compound 6 were determined according to Lara et al. (2010), detailed briefly below.

A two-fold micro-dilution assay was used to determine the MIC. MBCs were determined by sub-cultivation methods. The initial concentration of compound 6 was 6.5 mg/ml and the final dilution factor was 1:12. The bacterial strains were aerobically cultivated in sterile nutrient broth (Oxoid, UK) at 35° C. for 20 hours. The turbidity of the bacterial suspensions was 0.64 at 600 nm using a spectrophotometer. Each well of the 96-well microplates received 90 μL of sterile nutrient broth inoculated with 10 μL of bacterial suspension. In each row of each microplate, the first well received 100 μL of compound 6 solution (6.5 mg/ml compound 6) dissolved in sterile distilled water, and was well mixed. Then, 100 μL of the first well was transferred into the next well, which was well mixed in turn. This dilution process was repeated until the last well in the row was reached. 100 μL of the final well was moved from each row into a flask containing 70% ethanol solution. Blank treatments were performed using sterile nutrient broth, sterile nutrient broth inoculated with bacteria, and sterile nutrient broth with compound 6. The plates were aerobically incubated at 35° C. for 19 hours, and subjected to shaking at 200 rpm. To determine the MIC, the optical densities of wells at 630 nm were recorded using a microplate reader. To confirm results, all wells were subcultivated on Petri plates containing 20 ml of nutrient agar, and aerobically incubated at 35° C. for 24 hours. The resulting bacterial growth was observed. The concentration inhibiting 90% of bacterial growth is taken as the MIC, whereas the concentration inhibiting 100% of bacterial growth is taken as the MBC.

Example 3

Anticancer Activity Assays

HepG2, LoVo and MDA-MB-231 human cancer cell lines were cultured in Dulbecco's Modified Eagle Medium (DMEM) growth medium with 10% fetal bovine serum (FBS). The cytotoxic effect of compound 6 was determined by MTT ([3-(4,5-dimethylthiazol-2-yl)-2,5-diphenyltetrazolium bromide]) assays. In short, cells were seeded in a 24-well plate at a density of $5 \times 10^4$ cells/ml and incubated at 37° C. in 5% $CO_2$ incubator for 24 hours. On the following day, different concentrations (300, 150, 75 and 30 μg/ml) of compound 6 were prepared and added to the cells and the cells were incubated for an additional 48 hours. Methanol served as a control. Inhibition of cell proliferation was assessed by adding MTT reagent (100 μl of 5 mg/ml) and the reaction mixture was incubated for an additional 2 hours. Acidified isopropanol (isopropanol with 0.01 M HCL) was added to dissolve the resulting violet formazan. Absorbance values of formazan readings were measured at a wavelength of 540 nm using a microplate reader (Thermo Fisher Scientific, USA). Cell viability was calculated using the following formula:

% cell viability=(Absorbance of treated sample−Absorbance of control)×100

$IC_{50}$ values (i.e., the concentration of compound 6 that inhibits cell viability by 50%) were calculated from the observed dose dependence (FIG. 5A).

Example 4

Cytotoxicity Lactate Dehydrogenase (LDH) Release Assay

Cells from HepG2, LoVo and MDA-MB-231 human cancer cell lines were cultured in DMEM growth medium with 10% FBS. Cells were seeded in 24-well plates at a density of $5 \times 10^4$ cells/ml and incubated at 37° C. and 5% $CO_2$ in an incubator for 24 hours. The cultured HepG2, LoVo and MDA-MB-231 cells were then treated independently with compound 6 at $IC_{50}$ concentration for 48 h. The LDH released from treated cells was assessed by quantifying the amount of LDH activity in culture media using an LDH detection kit (Sigma Aldrich Inc., USA), according to the manufacturer's instructions. Briefly, 100 microliters of mixture reagent was added to an equal volume of cell culture medium and incubated in the dark at room temperature for 30 min. The absorbance was measured spectrophotometrically at 490 nm using a microplate reader (Thermo Fisher Scientific, USA) comparing treated cells to control cells treated with methanol.

Example 5

Larvicidal Assay

Larvicidal activity of compound 6 was determined for a susceptible strain of *Culex pipiens* reared in the Zoology Department of King Saud University. Mosquitoes were reared in the lab for 10 generations according to Ahmed et al. (1999) before performing experiments. Briefly, mosquitoes were reared in a plastic tray (24×35×5 cm) containing fish feed, at 27±2 C° and 50±5% relative humidity, and subject to a 14:10 light:dark photo-period. The mosquitoes were fed daily until they become pupae. Pupae were transferred from the trays to a cup containing tap water and were maintained in an insectary. Emergent adults were moved to a mosquito cage, where they were fed with a 10% glucose solution provided in a jar with a cotton wick. A filter-paper-lined glass petri dish with 100 ml tap water was kept inside the cage for oviposition. Different concentrations were prepared (75, 100, 150, and 200 μg/ml) from stock solution of compound 6. Each test solution was placed in multi-well plates (12 well) and dried in an oven at 40 C°. Then, one ml of tap water was added and tested against 10 of $4^{th}$ instar larvae. Each experiment was conducted in triplicate and tap water was used as a negative control (tap water) according to Almekhlafi (2018). The number of dead larvae was counted after 24, 48 and 72 hours of exposure and the percentage of mortality was reported for the average of three replicates. The LD50 and LD90 were calculated and reported in Table 10.

It is to be understood that the thiazole derivative is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A thiazole derivative compound having the formula:

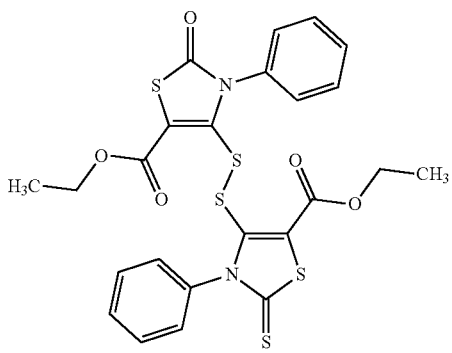 [SMILES: CCOC(=O)c1sc(=O)n(-c2ccccc2)c1SSc1c(C(=O)OCC)sc(=S)n1-c1ccccc1]

or a pharmaceutically acceptable salt thereof.

2. A pharmaceutical composition, comprising the compound according to claim 1 and a pharmaceutically acceptable carrier.

3. A method of treating a disease, comprising:
administering to a patient a therapeutically effective amount of the pharmaceutical composition according to claim 2, wherein the disease is selected from the group consisting of cancer and bacterial infection, wherein the cancer is selected from the group consisting of liver cancer, colon cancer and breast cancer and the bacterial infection is caused by *Staphylococcus epidermidis*.

4. The method of claim 3, wherein the bacterial infection is antibiotic resistant to at least one of amoxicillin, ciprofloxacin, clindamycin, daptomycin, erythromycin, fosfomycin, fusidic acid, gentamicin, Imipenem, levofloxacin, linezolid, moxifloxacin, mupirocin, oxacillin, rifampin, synercid, teicoplanin, tetracycline, trimethoprim/sulfamethoxazole and vancomycin.

5. A larvicidal active composition, comprising the compound according to claim 1 and at least one of a carrier, a diluting agent, a filling agent, and a surface active agent.

6. A method for inhibiting or preventing mosquito growth, comprising applying the larvicidal active composition of claim 5 to a locus infested by at least one of mosquitoes, mosquito larvae, and mosquito eggs.

7. A method of synthesizing a compound, comprising:
mixing diethyl 2,2'-(thiocarbonylbis(sulfanediyl)diacetate with phenyl isothiocyanate in an organic solvent to form a mixture; and
adding $K_2CO_3$ to the mixture to form a second mixture; and
adjusting a pH of the second mixture to form a compound having the structure:

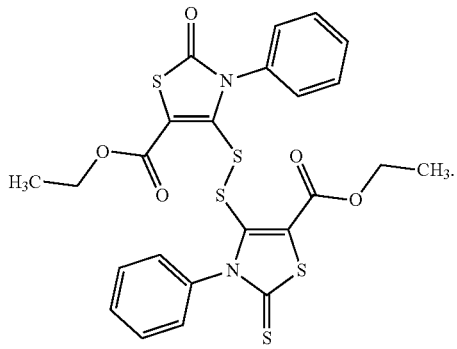 [SMILES: CCOC(=O)c1sc(=O)n(-c2ccccc2)c1SSc1c(C(=O)OCC)sc(=S)n1-c1ccccc1]

8. The method of claim 7, wherein the second mixture is stirred at room temperature for about 12 hours.

9. The method of claim 8, wherein the organic solvent is dimethyl formamide.

10. The method of claim 8, wherein adjusting the pH of the second mixture comprises adding aqueous HCl to the second mixture.

11. The method of claim 8, wherein the compound is in crystal form.

* * * * *